United States Patent
de Leij et al.

(10) Patent No.: US 7,417,137 B2
(45) Date of Patent: Aug. 26, 2008

(54) NON-SQUAMOUS EPITHELIUM-SPECIFIC TRANSCRIPTION

(75) Inventors: Lou Franciscus M. H. de Leij, Groningen (NL); Marcel Herman J. Ruiters, Groningen (NL); Pamela Marijke J. McLaughlin, Groningen (NL); Martin Conrad Harmsen, Eelde (NL); Henk van der Molen, Groningen (NL); Peter Terpstra, Groningen (NL); Willem Hendrik A. Dokter, Nijmegen (NL)

(73) Assignee: Synvolux IP B.V., Groningen (NL)

( * ) Notice: Subject to any disclaimer, the term of this patent is extended or adjusted under 35 U.S.C. 154(b) by 35 days.

(21) Appl. No.: 10/009,579

(22) PCT Filed: Feb. 28, 2001

(86) PCT No.: PCT/NL01/00166

§ 371 (c)(1),
(2), (4) Date: Mar. 26, 2002

(87) PCT Pub. No.: WO01/71015

PCT Pub. Date: Sep. 27, 2001

(65) Prior Publication Data

US 2002/0156041 A1    Oct. 24, 2002

(51) Int. Cl.
*C07H 21/04*   (2006.01)
*C12N 15/63*   (2006.01)
*C12N 15/85*   (2006.01)

(52) U.S. Cl. .................. 536/24.1; 435/320.1; 435/325
(58) Field of Classification Search ............. 536/34.1; 435/325, 320.1
See application file for complete search history.

(56) References Cited

FOREIGN PATENT DOCUMENTS

| WO | WO 98/00013 | 1/1998 |
|---|---|---|
| WO | WO 98/01350 | 4/1998 |

OTHER PUBLICATIONS

Chen et al. J. Clin. Invest., 1996. vol. 98, No. 11, pp. 2539-2548.*
Verma et al. (1997, Nature, vol. 389, pp. 239-242).*
Anderson et al.(1998, Nature, vol. 392, pp. 25-30).*
Palu et al.(1999, Journal of Biotechnology, vol. 68, pp. 1-13).*
Siemieniako et al (1992), BBRC, vol. 186, No. 3, pp. 1353-1361).*
M. Balzar et al, "The Biology of the 17-1A Antigen (Ep-CAM)", Journal of Molecular Medicine, vol. 77, No. 10, Oct. 1999, pp. 699-712.
B. Birren et al, "*Homo sapiens* Chromosome 4, clone RP11-77N9 mag 4, Working Draft Sequence, 13 unordered pieces", EMBL Database Entry AC018614; Accession No. AC018614, Dec. 16, 1999.
M. Fornaro et al, "Cloning of the Gene Encoding Trop-2, a Cell-Surface Glycoprotein Expressed by Human Carcinomas", International Journal of Cancer, vol. 62, No. 5, Sep. 4, 1995, pp. 610-618.
A.J. Linnenbach et al, "Retroposition in a Family of Carcinoma-Associated Antigen Genes", Molecular and Cellular Biology, vol. 13, Mar. 1993, pp. 1507-1515.
B. Siemieniako et al, "Nuclear Proteins from Capan-2 Cell Line Form Specific Complexes with the 17-1A Antigen Gene Promoter", Biochemical and Biophysical Research Communications, vol. 186, No. 3, Aug. 14, 1992, pp. 1353-1361.
R.H. Waterston, "*Homo sapiens* Chromosome 2 Clone RP11-295PS, Working Draft Sequence, 8 Unordered Pieces" EMBL database Online! Accession No. AC079775.

* cited by examiner

*Primary Examiner*—Celine X Qian
(74) *Attorney, Agent, or Firm*—Banner & Witcoff, Ltd.

(57) ABSTRACT

The invention relates to the field of cancer therapy and diagnosis, in particular of carcinomas. The invention provides an isolated and/or recombinant nucleic acid comprising a tissue specific promoter or functional fragment thereof allowing for expression of a nucleic acid of interest operably linked to said promoter or functional fragment thereof in a cancer cell wherein said expression in said cancer cell is essentially carcinoma selective.

11 Claims, 3 Drawing Sheets

Fig. 1

EGP-2 promoter sequences

```
              BglII
-3967.AGATCTAGAA TAGAGAGGGA TTTGCTGCAT AGTGGTTAAG GACTTTTACT CTTCATTCTA TATAAAGAC TTTTGTTTTC
-3887.TACTCATCTA TTACTTATGG GATAACAAAA ATTTTAGAA CTGGTAGTCT TTTTAGACAG AGTTTATATAT ATATATATAT
-3807.ATATATATAT ATATATTTTT TTTTTTTTTT CCGCCTCCTG GGTTCAAGTG ATTCCCTGC TTGTTGCCTC GGCTGGAGTG
-3727.CAATGGCATG ATCTCGCTC ACCACAACCT CATGCCCAGC TAATTTTAT ATTTTAGTA GAGACAGGTT TTCACCAGGT CAAGTATCTG
-3647.GAATTACAGG CATGTGCCAC TCCTGACCTC AAGTGATCCA CCCGCTTTGG CCTCCCAAAG TGCTGGGATT ACAGGCGTGA GCCACCATGC
-3567.GCTCTCAAAC TCCTGACCTC AATATTAATA AATGTGCTTA TAGAACTACA AABGATTCAC.AATTAAAACA TAAAACGAGT
-3487.CTAGCCTGAA AATTTTGAGC AAAGAATGAC GGTGTTAATG AGTACTAAA ATAAACAATA CCGGCCG[GTGCAGTGGCTCA p39^B
                                       Sp-1                            XmaIII
-3407.AATTTTGAGC CCCAGCACTT TGGGAAGCTG ATCACCTGAG GTCAGGAGTT CAAGACCAGC CTGGCCAACG
-3327.TGCCTGTAAT CGGTCTCTAC AAAATTAGCC GGGCGAGGTG GCAGGCGCCT.GTAATCACAG CTACTCGGGA
-3247.TAGTGAAACC CGGTCTCTAC TTGAACCCAG GAGGTGGAGG TTGCAGTGAG CTGAGAACAT GCCATTGTAC TCCAGCCTGG
-3167.GGCTGAGACA GGAGAATTGC CGGACACGGT GCTTGCACC TGTAATCCCA GCACTTTGGG
-3087.GTAACAAGAT TGAAACTCTA TCTTAAAAA CAAAGTCAGG AGATCAAGAC CATCCTGGCC AACTCTGTCT CAACTGAAAA
-3007.AGGCCGAGGC AAGAGGATCA CAAGTCAGG GGTGGGTGGT GCCTGTAATC CCAGCTATTC AGGAGGCTGA TTGCTTGAAC
-2927.TACAAAAATT AGCCGGGTGT TCCGCCAAGA TCATGCCACT GCACTGCAGC TTGGGTGACA GAGCAAGACC CCATCTCAAA
-2847.CCAAGAGGTG GAGGTTGCAG AGCCCTGGATC AGCCCGGGTGT GGTGGCTCAA GCCCGTAATC CC[AGCACTTTGGGAGGCTGA p39^R4-7
-2767.AAAAAAAAAA AAGAAAAAAT ACCCTGGATC ACCCTGGATC AAGACCAGCC TGACCAACAT GAGAAACCC CATCTCTACT AAAAATACAA
-2687.GGTGGGCAGA TCACCTGAGG TCACCTGAGG TCAGGAGTTC AAGACCAGCC TGACCAACAT CATTGTGTAC CAGACAACAA
-2607.AAAATTAGCC GGACGTGGTG GCACATGCTT GTAATCCCAG CTACTCAGGA GGCTGAGGCA GGAGAATTGC CTGAATCCGG
-2547.GAGGCGGAGG TTGTGGTGAG GTGAGATGAT GCCATTGCAC TCCAGCCTGG GCAACAAGAG CAAAACTCTG CCTCAAAAAA
-2447.AGAAAGAAAA AAAAAAAAGA AAGAAAAAGA CAAAGTCAGG GGATGTATAC TCAGATACAA TGAGTTCAGAG ATTAGTCTGG
                                                                      Ap-1
-2367.TATTTTGTCA TTTATTTAAT AATTATGCTT ACTCAATTCA CTT[TATTGTAATTAACAATA AATAGCTGTC CAGTTATAAG p39^R17-1
-2287.AAGATGAAGT TCTCCCGATT AGTAAACAG ATTAGACCT CAGAATGCAA CATTTTGCCA ATAAAGCCAC AATAACCAGT
-2207.TAGTTTATTC TTGGGAAAAG TATATGTAAT [GAAAACATC [GAAAACATC CAAAATTCAG CAGACAACAA
                           Ets
-2127.AAATCTGGTT AACTT[CTTCC JGATTTGTTA GTACTATTC[TTTTTTTTTT G TTTGTTGTT TTTTTTTTT GAGACGGAGT p39^R15-2
-2047.TTCGCTCTTG TTGCCCAGGC TGGAGTGCAA TGGCGAAATG TCGGTTCACT GCAACCTCTG CCTCCCAGGT TCAAGTGATT
                                               Sp-1
-1967.CTCCTGCCTC AGTCTCCTGA GTAGCTGGGA TTACAGGCGC[ CCGC]ACCAC GCCTGGCTAA CTTTTGTAT TTTTAGTAGA
-1887.GACGGGGTTT CACCATGTTG GCCAGGCTGG TCTCGAACTC CTGACCTTAG GTGATCC[GC CTCT]GGT TCCCAAAGTG
                                                                  Sp-1
-1807.CTGAGATTAC AGGCATGAGC CACCGTACCT GGCCTAAATA CCTTATTCA TATACCACGT GAAATTAAA TTATACAAAA
```

Fig. 1, contd.

```
-1727.CAAATTATAG AGGTACTTAG AACAGCATGA CTATTTACAT TAATCAACTT GCCGGCACTT CAACAGAATA CAACATAGAA
-1647.ATGATTGTTT TAATATAAAC ATAAGCTTTG ATTTGACATA TACTTGTAGA AATTAATCAA ACTTAGCTGA ATCTTAAAAT
-1567.TGCTTTTTTA CCTTTCTTCT TTTTTTTTA TTTTTTATT CGACTCTCTG GTTCAAGCGA TTCCCTGCC CTGTTGCCAG ACTGGAGTGC
-1487.AGCGGTTTGG TCTCGGCTCA CCGCAACCTC ACACCTGGCT ACTTTTTGTA TTTTAGTTG AGATGGGTTT CACCATGTTG GCCAGCTCCT GAGTAGCTGG
-1407.GATTACAGGT GCCTGCCACC CTGACCTTCG ATCTGCCCAC CTGTGCCCCC AGCAAGGTGC TGGGATTACA AGCATGAGCC ACCGTGCCCA
-1327.TCTCGAACTC GCCTTCTTTC CTCTTTAAA CTCTTACTTT TATGATTTCT TTAGTGGATA AAAAGCTTTT AAAAAATAGG TTACAATGAT
     Eis
-1247.GCCTTCTTTC CTCTTTTAA ACAATTAAAA ACATTTAAAA ACACTAAATA GTATATATAT GAAGTATTTA TAATTATTTT AATATTGTAA
     Eis
-1167.ATTACAGACTA ACAAAAATA TCAAAAATA ACATTAAAA ACACTAAATA GTATATATAT GAAGTATTTA TAATTATTTT AATATTGTAA
-1087.TAATATAGTG TGTTGTGATT TGAATTCATC TGCACGGAAA TCCTTTCTTT CTATTCCCCT ATAT[TTTCTT p39^E7-2
-1017.TCCGAAGCGT CATCAACATT TTGGTTCTTT AATAGTAACC AAAACCCCGAA ATCATCTCGG TTCTCAGTAT TTGGCTCTAT
-937.GGGAAGCTC TTTCTTTTCT TTCTTTTTGA GACGGAGTCT TGCTCCTGTC GCCCAGGCTG GAGTGTAATG
     Eis
-857.GCACGATCTC TGCTCACTGC AACCCTCAGCC TCCCCAGTAG CTGGGATTAC AGGCATGCGC CACCACGCCC GGCTAATTTT
                                                                                  Sp-I
-777.GTATCTTTA GTAGAGACGG CGGTTCTTCCA TGTTGGTCAG GCTGGTCTCG AACTTCAAAC CTCAGGTGAT CCGCCCGGCT CTTCAAGTGC p39^E4-1
     Eis                                                                         Sp-I
-697.CGGCCTCCC [AAAGTGCTAGG ATTACAGGCG TGAGCCACCG CGCTCAGCCT AATTATAAAG AAACACTCAT TTTCTTCCCA AGAGAGCCAA
-617.TAGAAATGCT TATGAAAACG TATTAAGAGT TATTATAAAG AAACACTCAT TTTCTTCCCA AGAGAGCCAA
-537.GATTCTCTCT TTCCCTTTCT TTCTTTTTT CTCTCTGCCTGT GTTTGTATT CCTTAGCCT CCTCCGGTTA TAAAAGCTCT CTATCCAGTT
     Eis                                                                Eis
-457.AAGGTCTTTT TTATAGTGTT CTGGAAAGGTT CCCCATTCCT CAAGGGCTTTCAGAGACAGCTTCCTCCGGTTA TCAGCACAGA p39^E11-1
-377.CCCGCACCCTC TCCCCCAGG GCCACCAAAG ATCCCTAACG CCGGCCATGA CGGCAAGCAC CTGGGGCGG GCGGAGCGGG
                                                                                Sp-I
-297.ATCTTCAAAC CTCCCACTCT CCTCCTGGAG CCACACCTGT GGAGAGGGGC TGCAGCGCCG CAGAGGTGAG AGGGGAGCCT ACTCACTCCC
     AP-1
-217.GCGCGCGGGC CCACACCTGT GGAGAGGGGC GCGGCCCAAC CACCAGCGGC CGCCGCGCGA CGCGGGAC CCGCCTCCGC GCTGCCCGGC GCAGCATGGC
-137.CCAACTCCCG GGCGGGGCAG CATCAACGAG CGCTCCGCGG CGCGTGGACTACTACGCAG AGTCCTTCGG CGAGCTGAGCACCTTCGACGC CGGCTCCTCG
                         Sp-I                    Sp-I                                         XmaIII
-57.[CGGCCAGGTCGGGCAGGTGTG CGCTCCGCGG CGCGTGGAC CGACGCGGAC CGGCGTGCCC CAGGCCTCGC GCTGCCCGGC GCAGCATGGC
                                                                                         Eis
+23.CGTCGGGGGA CCCCCCCTCG CCCCGCGCACG AGTCCCGGGC CCCTCCCGCG AGTCCCGGGC CCCCTCCCGCG GCGACGGCGAC CTTTGCCGGC AGTCAGGAA GGTGAGGCGC
+103.TGTCCCACTC CCGGCCGCACG AGTCCCGGGC CCCTCCCGCG AGTCCCGGGC CGGACGGCGA CTTTGCCGGC AGTCAGGAA GGTGAGGCGC
                             SacI                                                         Eis
+183.GCCCCCGCAG GTCCTCGCGT TCGGGCTTCT GCTTGCCGCG GCGACGGCGA CTTTGCCGGC AGTCAGGAA GGTGAGGCGC
+263.GGATTGGAGC AGAGTTGTGG AGCTGGGCTG GGCTGGGGG CA
```

NON-SQUAMOUS EPITHELIUM-SPECIFIC TRANSCRIPTION

The invention relates to the field of cancer therapy and diagnosis, in particular of carcinomas.

Carcinomas, as for example distinguishable from sarcomas, lymphomas, or melanomas, in general are the malignant counterparts or neoplasia derived from epithelia. Distinct carcinoma types are basal cell or squamous cell carcinoma of the oral, laryngeal or oesophageal mucosae; carcinomas of the intestines, such as gastric adenocarcinoma, small intestinal or colorectal carcinoma; cholangiocarcinoma; pancreatic carcinoma, lung carcinoma; prostate, testicular, mammary, cervical, ovarian and endometrial carcinoma, and so on.

Carcinomas are in general a difficult tumour-type to treat. Despite numerous improvements in radiological, chemotherapeutical and surgical techniques current treatments for metastatic malignant disease such as carcinomas are often ineffective. Therefore, new immuno-therapeutical and genetic strategies, which can enhance the selectivity of systemic therapy so that tumour response is increased without toxicity to normal tissue, have gained interest. For example, various tumour antigens, such as the human pancarcinoma associated epithelial glycoprotein-2 (EGP-2), also referred to as 17-1A or Ep-CAM, have been a target for immunomodulation. Antibodies to EGP-2, a transmembrane antigen, have been successfully used in patients for imaging of small cell lung cancer and for adjuvant treatment of minimal residual disease of colon carcinoma leading to an increased survival of this otherwise poorly prognosed disease. By reducing the size of antibodies to create so-called ScFVs, by humanising constant regions to lower the immunogenicity, by designing bispecific constructs to bring immune effector cells into contact with tumour cells, by fusing antibodies to cytokines, drugs, or gene delivery vehicles, or by developing vaccines to tumour antigens, a number of groups have enhanced the potential of anti-tumour antigen mediated immunotherapy. However, still efficacy of immuno-therapy has to be evaluated, and effective animal models for such evaluation are often lacking.

Another promising strategy against cancer is genetic pro-drug activation therapy which aims to use differences between normal and neoplastic cells to drive the selective expression of a metabolic suicide gene that is able to convert a nontoxic prodrug into its toxic metabolite. A well known suicide gene strategy comprises the use of thymidine kinase gene and for example gancyclovir. However, despite the availability of promising gene/prodrug systems a major impediment to the development of gene therapy treatments is the lack of suitable expression cassettes for directing selective transgene expression. In particular there is little or no information on how to achieve carcinoma specific or selective transgene expression.

The invention provides an isolated and/or recombinant nucleic acid comprising a tissue specific promoter, promoter/enhancer, or functional fragment thereof allowing for expression of a nucleic acid of interest operably linked to said promoter or functional fragment thereof in a cancer cell wherein said expression in said cancer cell is essentially epithelia or carcinoma selective in that expression in carcinoma related cancer or epithelial cells is clearly more prominent than expression in non-carcinoma related cancer or epithelial cells. Of course, its expression being essentially carcinoma-selective also has impact on its expression pattern in non-cancer cells. In one embodiment, the invention provides a nucleic acid comprising said promoter or functional fragment thereof allowing for mainly simple or non-squamous epithelium-specific expression in essentially adult or well-differentiated tissue, at least in tissue developed beyond the stage of embryonic development, of said nucleic acid of interest operably linked to said promoter or functional fragment thereof, thereby differentiating a promoter or functional fragment thereof from for example a tissue specific human keratin 18 promoter (Abe and Oshima, JCB 111:1197-1206) which includes hepatocytes, and thus avoiding the possibility of liver-failure due to tissue-specific transgene expression of for example a suicide gene regulated by such a K18 promoter.

Also, the promoter provided herein clearly differs from for example the hexokinase II gene promoter to drive the of a expression suicide gene in tumors (WO 98/13507) which is not is not restricted to or selective for carcinomas, but extends to be expressed in all tumor cells and beyond. In vitro, the expression of hexokinase II in tumor cells, such as AH310 hepatoma and HepG2, was, albeit higher than in normal cells, i.e. hepatocytes, not-selective for epithelial cancer cells. Consequently, suicide gene therapy, utilizing said promoter against a plethora of tumor types carries the intrinsic potential severe side effect of killing the normal counterpart cell type of which the tumor was derived, because many cell types express hexokinase II. Furthermore, several of the normal cell types will often be readily accessible for the gene therapeutic device, given that a "foolproof" gene-targeting vector system has to be developed yet, whereas a promoter as provided herein requires little or no targeting.

Similarly, the use of TNF-alpha to manipulate the expression of PKR (double-stranded RNA dependent protein kinase) with the aim to induce in apoptosis in tumor cells (WO 98/00013) is not restricted to carcinomas, but for example also shown to be the case for CEA expressing tumors, hepatoma, and Kaposi's sarcoma, which are clearly not of epithelial descent. Several of the TNF-induced promoters are known to show at least low levels of transcription in normal tissue cells, again presenting the risk of increased side effects (increased apoptosis in normal tissues). In addition, several tumor cell lines show decreased responsiveness to TNF-alpha in vitro and are thus less prone to apoptosis. In addition, vascular endothelial cells are sensitive to TNF-alpha and are in constant contact with the blood stream. Therefore, the risk exists that the PKR constructs could be taken up by these endothelial cells and subsequently express low levels of the enzyme. This causes local apoptotic lesions, which may present as vascular leakage (oedema) or other endothelial disturbances such as coagulation alterations.

An advantage of treating carcinomas as provided herein, especially using suicide gene-therapy, not only resides in the enhanced specificity (selectivity) for carcinomas, but also resides for example in the functional barrier formed by a basal membrane behind which the normal epithelial cells are located. In contrast, the carcinoma cells comprise a much more loose tissue, which not only is strongly vascularized, but is much more accessible for large (targeted) molecules.

In a preferred embodiment, the invention provides a promoter or functional fragment thereof derived from a EGP-2 gene. Being a so-called pan-carcinoma associated antigen makes the human epithelial glycoprotein-2 (EGP-2) suitable for use as target for immuno therapy and gene therapy strategies. Defined by for example the Mabs CO17-1, GA733-2, MOC-31 and 323/A3 this kb EGP-2 protein, also referred to as Ep-CAM or 17-1A, is encoded by the GA733-2 gene. EGP-2 is expressed on all epithelial tissue derived cancers like that of the breast, pancreas, gonads, gastrointestinal, respiratory, and urinary tract, more benign epithelial neoplasias such as polyps often have high EGP-2 expression as well, whereas expression in normal tissue is limited to the basolateral cell surface of simple epithelia. EGP-2 has been defined as a homophilic adhesion molecule, which expression is associated with active proliferation and a morphoregulatory role in organogenesis. Since the isolation of antibodies of EGP-2 in 1979, immunotherapeutical strategies using EGP-2 as a target have been developed and are at present, with limited success, used in clinical settings. Use of the EGP-2 protein's carcinoma specificity for the development of gene therapy strategies, however, has, until now, never been possible considering the fact that the regulatory sequences directing this specificity could not be isolated and characterised. Here we provide the isolation and characterisation of the 5' sequences from the GA733-2 gene and the identification of (preferably cis-acting) sequences needed for selective expression of heterologous genes in EGP-2 positive cells or cells functionally equivalent thereto, such as (non-human) animal cells expressing EPG-2 functional homologues. Expression of a nucleic acid of interest operably linked to a promoter or functional fragment thereof as provided by the invention is thus mainly restricted to normal adult non-squamous epithelium or neoplasias derived from epithelia, such as wherein said epithelium comprises lung, kidney, pancreas, testis, bile duct or intestinal epithelium and other not yet defined neoplasias derived thereof comprising carcinoma cells.

In a preferred embodiment, the invention provides an isolated and/or recombinant nucleic acid comprising a tissue specific promoter, promoter/enhancer, or functional fragment thereof allowing for expression of a nucleic acid of interest operably linked to said promoter or functional fragment thereof wherein said carcinoma cells comprise lung carcinoma cells.

In a much preferred embodiment, the invention provides a nucleic acid according to the invention comprising a nucleic acid or functional fragment thereof as shown in FIG. 1, in particular the invention provides a nucleic acid fragment as shown from about position −778 to about position −422, or as shown from about position −1113 to about position −422, or as from about position −2190 to about position −422, or from about position −778 to about position 0, or further extensions thereof, as for example shown in FIG. 1, where a tissue-specific functional fragment is given or a nucleic acid functionally equivalent thereto, said functional equivalent preferably comprising the necessary epithelial transcription sites to render the fragment tissue-specific.

In a preferred embodiment, said promoter or functional fragment thereof does not comprise a canonical TATA box or an atypical CAAT box, as for example is the case with most promoter sequences such as for example with GA733-1 promoter sequences (see Linnenbach et al., PNAS 86:27-31, 1989; also as discussed in Siemieniako and Wiland, Biochem. Biophys, Res. Comm. 186:1353-1361, however, providing a promoter or functional fragment or equivalent thereof according to the invention with such a box or boxes does not necessarily deprive it of its tissue specific nature.

In a preferred embodiment, the invention provides a nucleic acid derived from a mammal, such as an experimental animal as a mouse or rat, or, preferably derived from a human.

The invention further provides a nucleic acid according to the invention further comprising a nucleic acid of interest. For example, fusions of the EGP-2 promoter (if desired the 55 kb XhoI-XhoI fragment comprising an EGP-2 genomic region or functional fragments thereof such as a smaller 10 kb 5'-end fragment or approx. 3.5 kb XmaIII 5'-end fragment, see sites therein in FIG. 1) with nucleic acid encoding heterologous protein(s) are provided to drive its expression in a epithelium specific fashion. Such a nucleic acid of interest can for example be a reporter gene, or functional fragment thereof, such as a GFP or luciferase gene, for example providing candidate drug tests wherein compounds are screened for their activity to regulate or modulate promoter/enhancer sequences according to the invention, preferably in a tissue specific way.

Another example comprises a nucleic acid according to the invention further comprising an inducible or suppressible promoter or functional fragment thereof.

The invention also provides a nucleic acid according to the invention further comprising a suicide gene or functional fragment thereof. Several suicides genes are known and can be applied, in one embodiment of the invention, said suicide gene comprises a non-mammalian cytosine deaminase (CD) gene. Genetically modified cells that express the nonmammalian enzyme cytosine deaminase (CD) gene are able to convert the nontoxic prodrug fluorocytosine (5-FC) to the toxic metabolite fluorouracil (5-FU). 5-FU inhibits DNA synthesis during the S phase of the cell cycle. In addition to direct cytotoxicity to the transfected cells significant toxicity from the converted prodrug can be transmitted to adjacent cells. This gene/prodrug system can even compensate for the inability of vector systems that cannot transfect all cells of a tumor. In a preferred embodiment, the invention provides use of EGP-2 transcriptional regulatory sequences to regulate transient expression of the cytosine deaminase (CD) gene in EGP-2 expressing carcinoma cells. CD expression using these constructs correlated well with the expression of endogenous EGP-2 and demonstrated effective killing of the EGP-2 positive cells.

The invention furthermore provides a vector, such as a plasmid, clone, or gene delivery vehicle, such as a non-viral or viral vector, such as an adenovirus vector, comprising a nucleic acid according to the invention. Such gene delivery vehicles as provided by the invention are very useful in carcinoma therapy, or in therapy directed at non-squamous normal epithelial disease.

The invention for example provides a gene delivery vehicle according to the invention targeted to carcinoma cells which is useful for tumour-selective suicide gene therapy, such as a vector provided with an EPG-2/CD chimeric gene construct as provided herein, optionally, when so desired, to be used in combination with a pan-carcinoma specific (for example an EGP-2-specific) gene delivery system enhancing the safety and efficacy of vector based anti-cancer gene therapy approaches according to the invention even further.

In addition, the invention provides a host cell comprising a nucleic acid, a vector or a gene delivery vehicle according to the invention, such host cells for example being oocytes wherein a nucleic acid according to the invention has been introduced to generate an transgenic cell, cell-line or animal, but such host cells also providing target cells for candidate drug tests wherein compounds are screened for their activity to regulate or modulate promoter/enhancer sequences according to the invention, preferably in a tissue specific way, thereby allowing detection of carcinoma specific drugs from amongst a great variety of compounds, preferably having been derived at by combinatorial chemistry.

Furthermore, the invention provides an experimental animal comprising a cell according to the invention, such as for example derived from an oocyte as provided by the invention. The invention provides for example the isolation of the EGP-2 regulatory sequences and usage of these sequences to direct epithelial specific EGP-2 expression in mice in fashion with the situation in humans. In this EGP-2 expressing mouse model as provided by the invention EGP-2-specific tolerance was observed.

The invention furthermore provides a method for evaluating a possible treatment of disease comprising testing such treatment on a host cell or an animal according to the invention, in particular wherein said treatment comprises treatment of disease comprising non-squamous epithelium or wherein said disease comprises carcinogenesis. For example, the EGP-2 transgenic host cell and mouse provided here may serve as a model to study the biology of the EGP-2 molecule and to evaluate efficacy and safety of the variety of generated anti-EGP-2 based immunotherapeutical modalities influencing diseases. Not only evaluation of immune therapy is provided, said mice can also serve to evaluate gene therapy, especially gene therapy aimed at treatment of carcinomas, or serve to further evaluate drug treatment. Cells, cell-lines and animals, such as rats or mice as provided by the invention can also be used for carcinogenicity testing, for example by providing a nucleic acid comprising promoter or functional fragment thereof according to the invention with an additional nucleic acid of interest such as a nucleic acid encoding the large T antigen of the SV40 virus, or any other protein or fragment thereof involved in (the onset of) tumorgenesis, whereby a cancer prone host cell or experimental animal is provided, specifically suited for detecting carcinogenicity by detecting carcinoma development. Transgenic animals generated with such a construct develop spontaneous tumors derived from epithelial tissues as only in these tissues the large T antigen is expressed.

In another example, the EGP-2 promoter sequences are fused to generate epithelium tissue specific deleter mice which can be used to create epithelium specific gene knockout mice. For instance, fusion of the EGP-2 promoter with coding sequences of the cre recombinase is provided for the generation of transgenic mice. This yields a deleter line with which it is possible to generate knockout mice that specifically lack expression of the "knocked out" gene in epithelial tissues, provided this gene had loxP sites to enable the cre recombinase to excise the gene. Similarly, the combination of the EGP-2 promoter with the Cre-ER$^T$ fusion protein generates deleter mice in which the epithelium specific deletion of loxP insertions can be induced with 4-hydroxy-tamoxifen. The Cre-ERT protein is a tamoxifen-dependent derivative of the "normal" cre recombinase (R. Feil, J. Brocard, B. Mascrez, M. LeMeur, D. Metzger and P. Chambon (1996) PNAS 93:10887-90).

Also, a fusion of the EGP-2 promoter with the GFP (green fluorescent protein, or any other reporter protein) is provided to generate transgenic animals. Preferably this is the p39$^E$ construct that was used to determine to minimal epithelium specific promoter. These transgenic animals express a reporter such as GFP in an epithelium specific manner. The use in organ transplant models enable to study the fate of donor derived epithelial cells. This is an important topic in transplantation science, as it will shed new light on issues that concern transplant rejection.

The invention furthermore provides use of a nucleic acid, a vector or a gene delivery vehicle according to invention for the preparation of a medicament, in particular wherein said medicament is for the treatment of cancer, preferably a carcinoma. Such a medicament as provided by the invention may comprise a nucleic acid, a vector or a gene delivery vehicle according to the invention, but may also be derived from a drug found in a candidate drug test as identified above. Said medicaments find their use in a method for the treatment of cancer as provided by the invention, for example comprising administering to a patient a nucleic acid, a vector, a gene delivery vehicle or a drug according the invention.

The invention is further described in the detailed description without limiting the invention thereto.

DETAILED DESCRIPTION

Based on immunohistochemical data, EGP-2 mainly shows expression in normal adult and fetal epithelial tissues, by most it is even seen as a strictly non-squamous epithelial molecule in adult humans (Balzar et al., J. Mol. Med. 77:699-712, 1999). EGP-2 is detected at the basolateral cell membrane of all simple (especially glandular), pseudo-stratified, and transitional epithelia. In contrast, normal squamous stratified epithelia are negative for EGP-2. In adult human tissues no expression was found in mesenchymal, muscular, brain and neural tissues. Furthermore, no EGP-2 expression was detected in cells of lymphoid origin. The level of expression may differ significantly between the individual tissue types. In the gastro-intestinal tract, the gastric epithelium expresses very low levels of EGP-2. Expression levels are substantially higher in small intestine, and in colon EGP-2 is probably expressed at the highest levels among all epithelial cell types. Glandular epithelium of the gall-bladder express EGP-2 but the transitional epithelium (urothelium) of the bladder is only slightly positive. In the lower respiratory tract, bronchi, bronchioles, and alveoli are EGP-2 positive. In adult liver the bile ducts are EGP-2 positive, whereas hepatocytes are negative. Most epithelial cells of the kidney, such as cells of the proximal tubules, distal tubules, and ducts, express EGP-2. In pancreas EGP-2 expression has been detected in the ductal epithelium and acini. In skin, the sweat ducts and the proliferative zone of the hair follicle reveal EGP-2 staining, whereas keratinocytes and melanocytes are essentially negative. Within the basal layers of the epidermis some EGP-2 reactivity can be observed in the reserve cells, since mAb MH99 was reported to be reactive with some cells within the basal layer of skin keratinocytes. The glands of the endocrine system (thyroid, parathyroid, pituitary and adrenal glands) contain EGP-2-positive epithelium. In mammary glands, the ductal epithelium reveals relatively high levels of EGP-2 expression. EGP-2 expression is detected in most epithelial tissues of the female genital tract (ovaries, oviducts, cervix, and uterus). Normal endocervical glandular epithelium (both columnar and reserve cells) reveals high expression levels of EGP-2, whereas ectocervical squamous epithelial cells do not express the molecule. Some EGP-2 expression may be detected in the basal cells of morphologically normal ectocervical tissue, but only in areas bordering lesions of cervical intra-epithelial neoplasia. In tissues of the male genital tract, some of the epithelial cells in testis, epididymis, seminal vesicle, and prostate reveal EGP-2 expression.

EGP-2 is a marker for differential diagnosis and prognosis of several types of carcinomas. Active proliferation in a number of epithelial tissues is associated with increased or de novo EGP-2 expression. This is especially evident in tissues that normally reveal no or low levels of EGP-2 expression, such as squamous epithelium. At the early stages of neoplasias of the uterine cervix, de novo expression of EGP-2 is often observed in areas with atypical, undifferentiated cells of the squamous epithelium. Thus, in cervical intraepithelial neoplasia (CIN) grades I and II, the basal and suprabasal cells are EGP-2 positive, while grade III lesions reveal up to 100% positive cells in all layers of the squamous epithelium. Moreover, a clear increase in both the number of positive cells and the level of EGP-2 expression is observed during the progression from CIN I to CIN III. Expression of EGP-2 in atypical cells of CIN lesions correlated with the disappearance of markers for squamous differentiation and enhanced proliferation. In weak, mild and severe oral mucosal dysplasias high levels of EGP-2 expression were detected in basal and suprabasal cells with a clear border between EGP-2-positive dysplastic cells and EGP-2-negative normal epithelial cells.

In glandular epithelium of the gastrointestinal tract, one can observe a gradient of decreasing expression of EGP-2 from crypts to villae. The level of EGP-2 expression correlates with the proliferative activity of intestinal cells, and inversely correlates with their differentiation. Dysplastic or metaplastic proliferation corresponds to an increase (sometimes to very high levels) in EGP-2 expression. In gastric epithelium that normally expresses low levels of EGP-2, a strong expression of EGP-2 is observed in proliferative metaplastic lesions, such as intestinal metaplasia. Even in colon, where the epithelium expresses very high levels of EGP-2, the development of polyps is reported to be associated with an increased expression of the molecule. Hepatocytes are EGP-2-positive during embryonic development (week 8 embryos), but negative in adult liver. However, during liver regeneration processes cells that morphologically resemble precursor stem cells are EGP-2-positive, but, as they mature into hepatocytes, they again become EGP-2-negative. Dysplastic lesions of the bladder epithelium (urothelium) reveal increased EGP-2 expression as compared to normal urothelium.

BRIEF DESCRIPTION OF THE DRAWINGS

FIG. 1 depicts EGP-2 promoter (SEQ ID NO:5) analysis. The nucleotide sequence of the approx 4.2 kb BglII-SacII fragment was determined. The names of the generated deletions are at the right of the Figure: p39g47, p39E17.1, p39E152, p39E7 I, p39E[ ]1, p39EF1-1, p39E12-2 and p39E12-3. p39E was derived by cloning the approx 3.6 kb XmaIII restriction fragment. The end of each deletion is marked with "[". Putative transcription factor binding sites are marked Sp-1, Ap-1, Ets. The putative transcription start site is marked with a hooked arrow. Size markers depicted to the left of the Figure are relative to this putative transcription start site.

Figure 2:
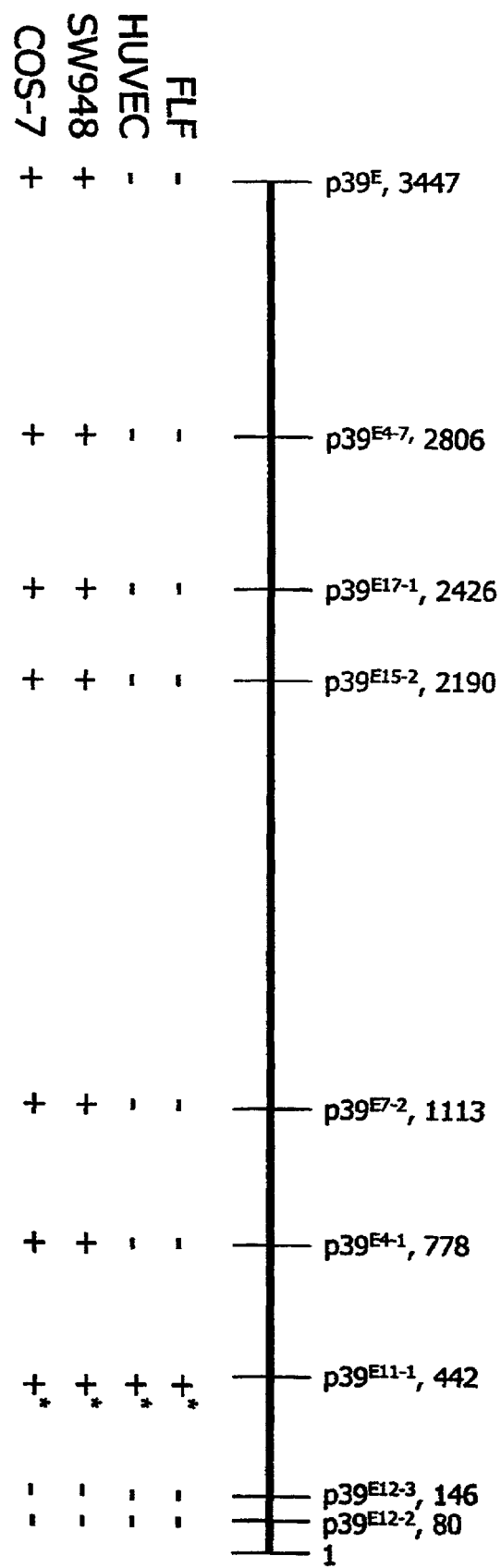
FIG. 2 depicts EGP-2 promoter analysis. Deletion mutants of the EGP-2 promoter were fused to enhanced green fluorescent protein and transfected into non-epithelial cells, i.e., human fetal lung fibroblasts (FLF) cells and human umbilical vein endothelial cells (HUVEC), or epithelial cells SW948 (human colorectal carcinoma), or as a transfection and expression control into COS-7 cells (immortalized kidney epithelial cells derived from the African green monkey). Construct names (corresponding to FIG. 1) are given above the line that represents the promoter. The numbers indicate the distance from the putative transcription start site that was given by Linnenbach et al (1993). In this Figure, the transcription start site is denoted as 1.

In human tissue EGP-2 is expressed only in epithelium and neoplasias derived from epithelia. Therefore, the molecule may be used as a marker to distinguish epithelial neoplasias from neoplasias derived from non-epithelial tissues. EGP-2-positive tumors are derived from epithelial cells, whereas EGP-2-negative tumors may originate from non-epithelial as well as epithelial tissues. Furthermore, EGP-2 may be used as a marker to histologically differentiate between epithelial neoplasias. Occasionally, difficulties in the histological differential diagnosis between basal-cell carcinoma (BCC) and squamous-cell carcinoma (SCC) of the skin may arise. Basal squamous cell epithelioma, a tumor combining morphological properties of BCC and SCC, is one common example of these difficulties, but other histological types of BCC may also be erroneously interpreted as SCC. Staining for EGP-2 demonstrated that all BCCs are diffusely and intensely labelled, whereas none of the SCCs expressed EGP-2, irrespective of the histological type or grade of differentiation. In liver neoplasias, EGP-2 was found to be expressed in almost all cholangiocarcinomas, whereas the majority of hepatocellular carcinomas were EGP-2-negative, suggesting that the hepatocellular carcinoma originates from a highly differentiated precursor. The results also indicate that EGP-2 can be used as an additional immunohistochemical marker to distinguish cholangiocarcinoma from hepatocellular carcinoma due to the differential expression in these epithelial tumors. Finally, it was demonstrated that EGP-2 can be used as a marker to discriminate carcinomas from EGP-2-negative mesotheliomas, except for the epithelioid types.

Malignant proliferation is nearly always associated with EGP-2 expression at some stage of tumour development. Most carcinomas, but no other tumour types, express high levels of EGP-2. However, EGP-2 expression in carcinomas can be heterogeneous, and is probably affected by a shift of tumour cell differentiation to either mesenchymal or squamous (in squamous carcinomas) cell phenotypes. It has been reported for dysplastic oral mucosa that well-differentiated squamous cell carcinomas are negative for EGP-2, whereas poorly differentiated squamous cell carcinomas are EGP-2-positive. Most squamous carcinomas are EGP-2-positive, except for (EGP-2-negative) squamous carcinoma of the skin. The expression of EGP-2 distinguishes squamous cell carcinoma of the skin from the EGP-2-positive basal cell carcinoma. Varying levels of EGP-2 expression were detected in the majority of squamous and adenocarcinomas of the uterine cervix.

The EGP-2 antigen has been suggested to be a homophilic adhesion protein, but the function of this protein is poorly understood (M. Trebuk et al., JBC (2001) 276 (3) 2299-2309). Transgenic mice have been used extensively to determine the function of proteins both in the development of diseases as for the evaluation of anti-disease therapies. However, although cloned in 1990, no suitable transgenic animal model expressing EGP-2 has been generated thus far, probably as a result of the fact that no appropriate regulatory sequences were available. Besides being expressed on most carcinomas, EGP-2 is also expressed on the baso-lateral cell surface of simple, transitional, and pseudostratified epithelia of the respiratory, gastrointestinal and urinary tract, the pancreas, gonads, and uterus/cervix, but not on hart, spleen, muscle, brain and connective tissue. When using EGP-2 as a target for immuno therapy there is a risk of side-effects induced by targeting to the antigen on this normal tissue. Indeed toxicity problems were observed after treatment with high-affinity anti-EGP-2 mAbs and a high affinity anti-EGP-2 mAb derived bispecific antibody. Thus, the relevance of an animal model to study immunotherapy targeting of the EGP-2 antigen for future use in patients is dependent on the expression of the antigen on normal animal tissues. Endogenous EGP-2 expressed by the mouse itself has been used to study anti-EGP-2 immunotherapy strategies however the immunotherapeutic molecule evaluated in wild type mice can not be used as a therapeutic in patients. Although the overall distribution of mEGP-2 is similar to human EGP-2, mEGP-2 expression was additionally observed in lymphoid organs like spleen and thymus and T-, B-, and dendritic cells. So results obtained in wild-type mice using mEGP-2 as a target may not hold true for humans. Although a transgenic mouse model expressing EGP-2 under the control of the mouse mammary tumour virus promoter and a transgenic rat model expressing EGP-2 under the control of the human keratin 18 regulatory sequences have been generated previously, the EGP-2 expression pattern observed in these transgenic animals did not resemble the human expression pattern.

Materials and Methods

Cell Culture

Both the human SCLC derived cell lines GLC-1 (EGP-2 negative) and GLC-45 (EGP-2 positive) (De Leij, 1985), as the human rectum adenocarcinoma cell line SW948 (EGP-2 positive) obtained from the ATCC (Rockville, Md.) (CCL 237), were cultured according to routine procedures in complete medium, i.e. RPMI 1640 (Gibco BRL, Paisley, UK) supplemented with 50 µg/ml Gentamycine Sulfate; 2 mM L-Glutamin; 1 mM Sodium Pyruvate (Gibco BRL); 0.05 mM α-mercaptoethanol (Biowhittaker) and 10% FCS (Bodinco) at 37° C. in humidified 5% $CO_2$ atmosphere. The SV40 transformed simian kidney cell line COS-7 also obtained from the ATCC (CRL 1651) and the primary human fetal lung fibroblasts (FLF) were cultured in DMEM (Gibco BRL) supplemented with 50 µg/ml Gentamycine Sulfate (Biowhittaker); 2 mM L-Glutamin (Gibco BRL); 10% FCS at 37° C. in humidified 5% $CO_2$ atmosphere. Endothelial cells were isolated from human umbilical veins (HUVEC) and cultured in RPMI 1640 supplemented with 20% heat-inactivated human serum, 2 mM L-Glutamin, 5 U/ml heparin, 50 µg/ml EC growth factor, 100 µg/ml streptomycin and 100 U/ml penicillin in 1% gelatin coated tissue culture flasks (Costar) at 37° C. in humidified 5% $CO_2$.

Cell Transfection:

The adherent cells were transfected by either the Saint (Saint Inc., Groningen, The Netherlands) or the FuGENE-6 (Boehringer-Mannheim, Dusseldorf, Germany) method. 1 day prior to transfection 6-wells plates (Costar) were seeded with $1-3\times10^5$ cells/well. The cells were transfected per well by 3 µl FuGENE-6 in 100 µl serum-free medium added to 0.5 µg DNA, which was subsequently dropwise added to the cells in standard culture medium. Or the cells were transfected, after washing twice with HBSS (Gibco BRL), with 33 µl 0.75 mM Saint in 100 µl HBSS added to 0.5 µg DNA in 100 µl HBSS completed to 1 ml with serum free medium of choice per well. After 3-4 h. incubation with this Saint-DNA serum free medium 2 ml standard culture medium was added. 24 h. irrespective of the transfection method used the cells were harvested by detaching them from the surface by trypsin/EDTA (0.5/0.2 mg/ml) in PBS and prepared for further analysis.

Isolation of the GA733-2 Promoter Region

For the isolation of the GA733-2 5'sequences, a BAC genomic library was screened commercially by GenomeSystem, Inc. (St. Louis, Mo., USA) with a 920 bps [$^{32}$P]-labeled genomic DNA fragment containing approximately 250 bp of the 5' region of the human EGP-2 gene GA733-2 in addition to the exons 1, 2, and 3. The probe was derived from the GA21726-22RS vector, kindly provided by Dr. Linnenbach (Wistar Institute, Philadelphia, USA), by digestion with SalI/SacII. DNA from the one positive clone was purified according to standard methods for BAC DNA isolation and analyzed by restriction mapping and Southern blot analysis.

Southern Blot Analysis

Since a SacII restriction site was present 39 bp downstream of the ATG, digestions with either SacII alone or in combination with; HindIII, EcoRI, BamHI, PstI, XbaI, BglII, EcoRV, SmaI, and XhoI (All obtained from Boehringer-Manheim) were carried out. After separation on a 0.8% agarose gel the DNA was transferred to a hybond N+ nylon transfer membrane (Amersham, Bucks, UK) and subsequently hybridized with the above described [$^{32}$P]dCTP labeled SalI/SacII EGP-2 promoter probe at 65° C. for 18 h in 1 mM EDTA, 0.5 M $Na_2HPO_4$ (pH 7.2), and 7% SDS. Membranes were washed once in 2×SSC, 0.1% SDS; once in 1×SSC, 0.1% SDS; 0.3×SSC, 0.1% for 1 h at 65° C. and visualized and quantified by autoradiography. A 4.2 kb spanning SacII/BglII genomic subfragment containing at least exon 1 and approximately 4 kb upstream sequences (4.2 kb EGP-2 promoter fragment) was identified and isolated from the BAC vector and cloned into the SacII/BamHI sites of the pBluescript SK plasmid (Stratagene, Inc., San Diego, Calif.). This construct was then subjected to further restriction mapping and DNA sequence analysis.

DNA Sequence Analysis

DNA sequencing was performed using the Thermo Sequenase cycle sequencing kit (Amersham-Pharmacia, biotech.) with Cy5 labeled primers (Eurogentec) on the ALF-express sequencer (Amersham Pharmacia, biotech.). DNA sequence data were managed and analyzed by the DNA Star computer program (DNA Star Inc., USA). Consensus sequences of transcription factor binding sites were identified using MacVector and by searching the TRANSFAC v3.2 database using Transcription Element Search Software (TESS, Pairwise sequence alignments were performed using the FASTA programs ALIGN and LALIGN.

GFP and Luciferase Plasmid Construction and Assays

The 4.2 kb EGP-2 promoter fragment was digested with XmaIII and subcloned into the NotI site of the pBluescript KS vector (Stratagene, Inc., San Diego, Calif.) generating two different constructs containing the insert in both orientations. By digestion with SacI/XhoI the fragment was cloned from one pBluescript construct into the GFP reporter plasmid pEGFP-1 (Clonetech, Palo Alto, Calif., USA), while by digestion with XhoI/SacII from the other pBluescript construct the same EGP-2 promoter sequence was cloned into the luciferase reporter pGL3 enhancer vector (Promega Inc., Madison, Wis., USA). The 3.6 kb promoter sequence cloned into these reporter vectors starts from −83 to −3508 containing the transcription start site and putative binding sites for Sp1 and AP-1 in the 5' untranslated region of exon 1 but not the ATG. Deletion constructs of the 3.6 kb EGP2 promoter region containing pEGFP-1 vector further referred to as p39$^E$, were generated using the double-stranded Nested Deletion Kit form Pharmacia (Amersham-Pharmacia, Biotech.). 22 constructs were generated following the manufacturers protocol using BglII to generate the recessed 3'-ends which were filled in with thionucleotides to make them nuclease resistant and SpeI to create a 5'-overhanging nuclease-sensitive end. The generated constructs chosen to be used in transfection experiments were; p39$^E$ (−3508/−83); p39$^{E4-7}$ (−2898/−83); P39$^{E7-1}$ (−2411/−83); p39$^{E15-2}$ (−2168/−83); p39$^{E7-2}$ (−1211/−83); p39$^{E9-2}$; p39$^{E4-1}$ (−871/−83); P39$^{E7-3}$; P39$^{E11-1}$ (−533/−83); P39$^{E12-3}$ (−238/−83), and p39$^{E12-2}$ (−170/−83). The numbers between the brackets refer to the positions towards the ATG in the GA733-2 genomic clone. GFP expression was studied both by microscopic and flow cytometric analysis using the Leica Quantimed 600 (Leica, Rijswijk, The Netherlands) and the Coulter Elite Cytometer (Coulter Electronics, Hilaleah, Fla., USA). Luciferase activity was measured using the Promega luciferase assay system (Promega Inc., Madison, Wis., USA) and light output recorded by the Anthos, Lucy 1 luminometer (Anthos labtec instruments, Salzburg, Austria).

EGP-2-EGP-2 and EGP-2-CD Constructs

The −83 to −3508 EGP-2 promoter region was cloned upstream of the EGP-2 cDNA by exchanging the luciferase gene of the pGL3 vector for the EGP-2 cDNA in which the EGP-2 promoter had already been cloned as described above. Furthermore this EGP-2 promoter region was cloned as a SpeI/NheI fragment upstream of the *E. coli* Cytosin Deaminase DNA, situated in NheI/PmeI sites of the pcDNA 3.1$^{(+)}$ (Invitrogen).

Generation of EGP-2 Transgenic Mice

A 55 kb XhoI DNA fragment containing the human EGP-2 gene was isolated from a BAC clone (Genomesystems Inc, St. Louis, Mo.). This genomic BAC clone was identified using 920 bps of the 5' region of the human EGP-2 cDNA derived from the GA21726-22R vector, kindly provided by Dr. Linnenbach (Wistar Institute, Philadelphia, USA).

The presence of GA733-2 genomic sequences was determined by PCR of exon 2-3, sense strand, 5'-ATAATAATCGT-CAATGCCAGTGTA (SEQ ID NO:1), antisense strand 5'-ATCATAAAGCCCATCATTGTTCT (SEQ ID NO:2) and exon 9 (sense strand 5'-TCAGATAAAGGAGATGGGT-GAGA (SEQ ID NO:3), antisense strand 5'-GGCAGCTTTCAATCACAAATCAG (SEQ ID NO:4). Restriction analysis and subsequent Southern blotting using the upstream SacII/SalI fragment or the 1.5 kb EGP-2 cDNA as probe it was set that at least 10 kb upstream and 4 kb downstream regulatory sequences were present. The 55 kb DNA fragment was introduced into oocytes of FVB/N mice according to standard methods. Three mice were found positive by PCR and Southern blot analysis for the EGP-2 transgene. Of these founders, two lines transmitted the transgene to their progeny. Both lines were fertile and healthy and expressed the EGP-2 protein and one line was selected for further studies. For investigation of tumor growth and humoral immunity the EGP-2 transgenic FVB/N mice were crossed with C57/B16 wild type mice.

Immunohistochemical Analysis

Tissue-culture supernatant of the hybridoma MOC31 (anti-EGP-2; IgG1) was purified by protein A column chromatography (Pharmacia, Uppsala, Sweden) and biotinylated. Immunoperoxidase stainings were performed on 5-µm-thick, air-dried cryosections made from snap frozen biopsies. After acetone fixation and rehydration, antibody was applied and incubated at room temperature for 1 h.

Cell Lines

The murine B16.F10 melanoma (ATCC) and the EGP-2 transfected B16.F10 melanoma, B16.B16.C215 kindly provided by Dr. Dohlsten, were maintained in DMEM (Gibco BRL, NY, USA) supplemented with 50 µg/ml gentamycin sulfate (Biowhittaker, Vervier, Belgium); 2 mM L-glutamine (Gibco BRL); 10% FCS (Bodinco, Alkmaar, The Netherlands) at 37° C. in humidified 5% $CO_2$ atmosphere. The human EGP-2 expressing rectum adenocarcinoma cell line SW948 (ATCC) was cultured as above and used to score antibodies in the serum of mice.

Tumor Induction

Subcutaneous tumors were induced by s.c. injection of $5 \times 10^5$ B16.F10 or B16.B16.C215 cells in the right or left flank of trangenic mice or non-transgenic controls. Tumor development was determined by palpation at 14 to 21 days after induction.

Antibodies

Undiluted tissue-culture supernatant of the anti-EGP-2 hybridoma MOC31 (IgG1) was used to identify the presence of EGP-2 both immunohistochemically as well as on Western blot. An anti-bacterial cytosine deaminase antibody kindly provided by Dr. Haack, Heidelberg, Germany was used to identify CD positive cells immunohistochemically in a 1:50 dilution. The anti-GFP polyclonal antibody was obtained from Molecular Probes, Eugene, Oreg., USA and diluted 1:200. Horseradish-peroxidase-conjugated rabbit anti-mouse Ig and goat anti-rabbit Ig (Dakopatts, Glostrup, Denmark) were used to detect the specifically bound antibodies.

SDS-PAGE and Western-Blotting

Detection of the human EGP-2 protein was performed on cell lysates. The cells were homogenized in 250 µl, 250 mM Tris-HCL (pH 7.8), after which protein was further extracted by 5-times freeze/thaw cycling. Protein concentration was determined by the method of Bradford (41) (Bio-Rad Laboratories) on serial dilutions of the lysates. 12 µg protein was mixed with an equal volume 2×SDS-PAGE sample buffer (42) without 2-mercapto-ethanol and heated at 100° C. for 5 min. SDS-PAGE (42) was performed using the BioRad miniprotean II system with 10% polyacrylamide gel. Samples were semi-dry electroblotted onto nitrocellulose filters (Amersham, Chalfont, UK). After blotting, the filters were blocked overnight with 5% nonfat dried milk in PBS supplemented with 0.1% Tween-20. Filters were incubated with MOC31 hybridoma supernatant, washed, after which specific binding of the antibody was visualized using the ECL detection kit of Amersham, Chalfont, UK.

Immunohistochemistry

Cytospin slides of acetone-fixed cells were evaluated for EGP-2, CD, or, GFP expression by incubating with the relevant antibody at RT for 1 h. Peroxidase-conjugated rabbit anti-mouse or goat anti-rabbit Ig, diluted 1:50 in PBS containing 1% normal serum, in combination with 0.01% H2O2 and AEC (Sigma, Bornhem, Belgium) as substrates, were used for specific staining. Counter staining was performed using a Mayers hematoxylin solution (Merck).

Results

We isolated a BAC clone containing the 14 kb GA733-2 genomic sequences including its own 10 kb upstream and at least 30 kb downstream regulatory sequences as determined by Southern blot analysis and PCR. Screening of a BAC genomic library with a 5' GA733-2 probe yielded one positive clone, which was characterized by restriction enzyme mapping, PCR-screening, and nucleotide sequencing. To define the GA733-2 promoter region, restriction analysis with SacII and double digests with SacII and a number of other enzymes were carried out. Since a SacII site is positioned ~40 bp downstream of the ATG it was determined by Southern blot hybridization with the 5' GA733-2 probe that the BAC clone contained at least 10 kb of GA733-2 upstream sequences (SacII digestion alone). Digestions with SacII and EcoRV or SacII and BglII revealed bands containing exon 1 and approximately 5 or 4 kb of upstream sequences, respectively (EcoRV, BglII digestion). The SacII/BglII fragment was isolated, cloned, and further analyzed.

Sequencing of the cloned SacII/BglII 5' GA733-2 promoter region in both directions yielded ~4 kb of sequence upstream of the longest reported 5' untranslated region of the EGP-2 cDNA (Salza) (FIG. 2). This upstream region lacked canonical TATA and CAAT boxes commonly found within 100 bp upstream of the putative transcription sites. The 5'-upstream sequences did contain several putative cis-acting regulatory elements.

The complete nucleotide sequence of the approx 4.2 kb BglII-SacII fragment was determined. Exonuclease (Nested Deletion Kit from Pharmacia) was used to generate deletions from the 5' end of the promoter. The deleted promoter clones were also sequenced. The names of the generated deletions are mentioned to the right of the FIG. 1: $p39^{E4-7}$, $p39^{E17-1}$, $p39^{E15-2}$, $p39^{E7-2}$, $p39^{E4-1}$, $p39^{E11-1}$, $p39^{E12-2}$ and $p39^{E12-3}$. $p39^E$ was derived by cloning the approx 3.6 kb XmaIII restriction fragment. Putative transcription factor binding sites are marked (Sp-1, Ap-1, Ets) in FIG. 1, of these Ets is a known epithelium specific transcription factor (B. Wasylyk, S. L. Halm and A. Giovane (1993) The Ets family of transcription factors. Eur. J. Biochem. 211:7-18). In addition, Sp-1 in combination with a Ets binding site in close proximity is known to regulate epithelium specific gene expression (J. H. Lee, S. J. Jang, J. M. Yang, N. G. Markova and P. M. Steinert (1996) The proximal promoter of the human transglutaminase 3 gene, J. Biol. Chem. 271:4561-4568). The previously published sequence by Linnenbach et al (Mol. Cell. Biol. (1993)13, 1507-15, genbank accession M93029) is boxed at the bottom of the figure. Of this sequence the cDNA is given in italics, whilst the protein encoding sequence (starting with ATG) is given in bold italics. The putative transcription start site, as was suggested by Linnenbach et al is marked with a hooked arrow.

The epithelial glycoprotein 2 (EGP-2), also known as Ep-CAM or the pancarcinoma associated protein 17-1A, encoded by the GA733-2 gene, is expressed as a stable transmembrane protein at high levels on the surface of most carcinomas. Despite the fact that EGP-2 is also expressed on normal simple epithelial tissue, EGP-2 is regarded as an attractive target for anti-cancer immunotherapeutical treatment strategies. To explore the mechanisms regulating the expression of the EGP-2 gene, 3.6 kb of sequences upstream from the transcription start site were assessed for their ability to control the expression of the EGP-2 cDNA, the green fluorescent protein (GFP), and the luciferase reporter genes. Analyses of the expression of these constructs in transiently transfected EGP-2 positive and EGP-2 negative carcinoma and non-carcinoma derived cell lines revealed epithelial specific expression. Deletion analyses defined a basic proximal promoter region, which for example confers epithelial-specific expression to the GFP reporter gene. Using these sequences to direct the prodrug 5'CU converting enzyme cytosine deaminase it was possible to discriminate between EGP-2 expressing and non-expressing cells by the cytotoxic effect of the drug. As these EGP-2 sequences confer promoter/enhancer activity to reporter genes in a tissue specific manner, they are useful for gene therapy in EGP-2 overexpressing carcinomas.

By injecting a 55 kb GA733-2 spanning genomic DNA fragment isolated from this BAC clone into FVB/N mice oocytes, fully immunocompetent mice transgenic for the human EGP-2 protein were generated. Expression of the human EGP-2 protein in the generated transgenic mice was confined to the lung, kidney, pancreas, stomach, colon, small intestine, gonads and not to the hart, muscle, brain, spleen, and liver tissue in two EGP-2 transgenic mice lines as determined by RT-PCR and Western blotting. Immunohistochemical analysis revealed that the EGP-2 promoter sequences directed the EGP-2 expression to the membrane of corresponding epithelial cells revealing a distribution pattern similar to the human situation. In the kidney strong EGP-2 expression was observed in the epithelial cells of the Henle's loop whereas the Bowman's capsule and the proximal and distal tubuli stained weakly positive. The stratified bronchial epithelium of the major airway, the alveolar epithelium and epithelial tissue found in the mucus glands of the broncheal mucosa stained also positive for EGP-2 expression. Of the gastointestinal tract the villus and crypt epithelium of small intestine and colon as well as the gastric surface epithelium of the stomach demonstrated EGP-2 expression whereas the gastric glands appeared to be negative. EGP-2 expression was also observed in the glandular epithelium of the endometrium, the tubuli seminiferi of the testis and in the valopian duct epithelium of the ovary. Furthermore, the exocrine and ductular epithelium of the pancreatic tissue stained positive for EGP-2, whereas the endocrine epithelial stained only weakly positive. In the liver EGP-2 expression was observed in the bile duct epithelium, whereas the hepatocytes were negative and in the thymus epithelia with especially the Hassall's corpuscles stained positive for EGP-2. No EGP-2 expression was observed in hart, muscle, spleen and T-, B, and dendritic cells nor was EGP-2 shed in the blood as determined by immunohistochemical and FACS analysis. This observed transgene expression pattern was integration site-independent but copy number dependent as established by FISH analysis (results not shown).

The human EGP-2 protein consists of an extracellular domain with two EGF-like repeat motifs, a transmembrane region of 23 hydrophobic amino acid residues, and a relatively short 26-residue highly charged cytoplasmic domain with an internalization motif. Upon transfection with EGP-2, cells incapable of intercellular adhesion formed aggregates suggesting a homotypic adhesion function for EGP-2. Several other experiments pointed to a role of EGP-2 as signaling molecule leading to a regulation of proliferation and differentiation of epithelial cells and also a morphoregulatory role was credited to the EGP-2 protein. However, the exact role of EGP-2 in epithelial cell functioning remains to be elucidated. The high-affinity mAb MOC31 recognizes an epitope in the first EGF-like repeat of the extracellular domain of the EGP-2 molecule. Specific MOC31 mAb binding to EGP-2 expressed on the membrane of the normal epithelial tissues of the EGP-2 transgenic mice and comparison of this staining pattern with the MOC31 staining pattern of human EGP-2 expressing normal epithelial tissues demonstrated an accurate expression of the transmembrane glycoprotein in this EGP-2 transgenic mouse model. However, though being defined as a homotypic adhesion molecule, no evidence of adhesion was observed in the EGP-2 transgenic mice. Survival was identical in EGP-2 transgenic mice and wild-type mice as analyzed for 12 months, despite expression of EGP-2. Additionally, strong expression of EGP-2 on the ovary duct and sertoli cells did not influence fertility of the transgenic animals. Transgenic female animals gave normal birth to viable transgenic offspring. These observations debate the function of EGP-2 as a homophilic adhesion molecule. This function, however, was established in cells lacking their own means of cell-cell interactions and not in the presence of mEGP-2. The presence of mEGP-2 can also explain why other functions ascribed to EGP-2 are not observed, like active proliferation, whether normal or neoplastic. No neoplastic lesions or morphological aberrations were observed in the EGP-2 transgenic mice tissues analyzed, suggesting a bystander role of the EGP-2 protein in these processes. However, in the mammary gland of the MMTV-EGP-2 transgenic mice ductal hyperplasia was observed and differentiation of lobular and ductal cells was affected by the ectopically expressed human EGP-2. The observed differences between these EGP-2 transgenic mice models might be explained by the differences in 5' regulatory sequences or intron specific regulatory elements used as has been described for several transgenically expressed genes and promoters.

Since EGP-2 is one of the best-studied tumor-associated antigens frequently used as a target for experimental and clinical cancer immunotherapy, we wanted to induce human EGP-2 positive cancer in our transgenic mice. Previously the B16.F10 murine melanoma cell line has been stably transfected with the GA733-2 cDNA and was called B16.C215. This cell line was then used to study the role of antibody-targeted super antigens in immunotherapy in animal models mimicking human malignant conditions (Dohlsten 1995). To adept this C57/B16 model on the current EGP-2 transgenic FVB/N mice, transgenic FVB/N/C57/B16 hybrid mice were generated and tumor growth was monitored after subcutaneous induction of EGP-2 positive B16.C215 or EGP-2 negative B16.F10 tumors. The EGP-2 expression pattern remained the same in the hybrid genetic background as was established by immunohistochemical analysis (results not shown). No significant difference in growth of the s.c. induced B16.F10 or B16.C215 tumors was observed between EGP-2 transgenic mice or wild-type littermates. However, approximately 60% of the transgenic animals demonstrated intraperitoneal growth of the B16.C215 tumor upon s.c. induction. This intraperitoneal invasive growth was not observed in nontransgenic animals or in transgenic animals upon s.c. induction of a B16.F10 tumor in 3 independent experiments with 4 animals per condition. Tumor growth in the peritoneal cavity surrounded but never invaded the organs present and was associated with an increased lethality among the transgenic animals s.c. injected with B16.C215 tumor cells (3b). Another striking difference between transgenic and nontransgenic animals upon tumor induction was the observed spleen enlargement in wild-type animals. This spleen enlargement could only be observed in transgenic animals in relation to intraperitoneal growth. To investigate the meaning of this observed spleen enlargement blood serum of all animals was tested on anti-EGP-2 reactivity using constitutively EGP-2 expressing human cells and as a control EGP-2 negative human cells. An anti-EGP-2 humoral immune response was observed in the non-transgenic mice whereas no such response could be observed in the serum of the EGP-2 transgenic mice. However, no spleen enlargement was observed in the transgenic animals upon induction with B16.F10 cells as well demonstrating a complete tolerance, irrespective of the transgene, which is not associated with enhanced tumor growth. This is interestingly since both the B16 melanoma cells and the EGP-2 protein, are considered poorly immunogenic. B16 mouse melanoma cells are poorly immunogenic due to expression of only minute amounts of MHC class 1 molecules (Dohlsten, 1995), whereas the high degree of EGP-2 with its murine homologue is responsible for its poor immunogenicity in mice. Also in humans EGP-2 is found to be poorly immunogenic. About 15% of colorectal carcinoma patients had IgG autoantibodies against EGP-2, while no healthy donors examined did. Although the frequency was higher with more advanced clinical stage, no significant association between the presence of auto-EGP-2 antibodies and survival was noted.

This seemingly paradigm between EGP-2 expressed by the transgenic animal demonstrating no relation between EGP-2 expression and proliferation or neoplasia and the EGP-2 expressing B16.C215 tumor cells which demonstrate enhanced invasive properties in comparison to its parental B16.F10 cells in EGP-2 transgenic mice was observed previously in several experiments. Using both human tissue culture cells and animal models it was established that (over-) expression of EGP-2 correlated with both benign and malignant proliferation of epithelial cells. The EGP-2-transgenic mouse tumor-model presented here seems to be an excellent tool to study this dualistic role of EGP-2 in tumor development and the additional signals responsible for either phenotype. Specifically when these EGP-2 transgenic mice are cross-bred with mice that are genetically predisposed to develop different types of tumors. In addition, since the endogenous EGP-2 regulatory sequences have been used to direct EGP-2 expression in these transgenic mice they can also be used to evaluate the importance of EGP-2 during embryonic development or morphogenesis of individual tissue. Though relatively little information is available concerning the expression of the EGP-2 gene during human embryonic development, several studies suggest an important role for EGP-2 during embryogenesis. EGP-2 is expressed by the majority of human epithelial neoplasias, and as such has been a target for immuno- and gene therapy strategies. Anti-cancer strategies targeting the EGP-2 antigen require an appropriate pre-clinical model to study the efficacy and toxicity of these strategies in order that in the near future strategies targeting this molecule can be applied safely in clinical trials to combat carcinomas in patients. The EGP-2-transgenic mouse tumor-model provided here is an excellent tool to study these new therapeutic strategies. Not only does it express the human EGP-2 protein accurately and with a distribution pattern similar to the pattern seen in humans (Table 1), but it displays also the immunological tolerance frequently observed in cancer patients against tumor antigens. This is of great significance since the mechanisms that regulate immunological tolerance to tumor antigens are formidable obstacles that withstand effective tumor immunotherapy in cancer patients.

TABLE 1

Epithelal glycoprotein-2 (EGP-2) distribution in EGP-2 transgenic FVB/N mice

| Tissue | Transgenic mice | | | Nontransgenic mice | | |
|---|---|---|---|---|---|---|
| | MOC31[bio] | UBS 54 | PBS | MOC31[bio] | UBS 54 | PBS |
| Liver (Bile duct) | + | + | − | − | − | − |
| Liver (Hepatocytes) | − | − | − | − | − | − |
| Pancreas | + | + | − | − | − | − |
| Small intestine | + | + | − | − | − | − |
| Colon | + | + | − | − | − | − |
| Lung | + | + | − | − | − | − |
| Kidney | + | + | − | − | − | − |
| Stomach | + | + | − | − | − | − |
| Gonads | + | + | − | − | − | − |
| Thymus(Hassall's corpuscles) | + | + | − | − | − | − |
| Brain | − | − | − | − | − | − |
| Heart | − | − | − | − | − | − |
| Skin | − | − | − | − | − | − |
| Spleen | − | − | − | − | − | − |
| Muscle | − | − | − | − | − | − |

Figure Legends

FIG. 1

EGP-2 Promoter Analysis

Nucleotide sequence of the approx 4.2 kb BglII-SacII fragment was determined (SEQ ID NO:5). The names of the generated deletions are mentioned to the right of the figure: p39$^{E4-7}$, p39$^{E17-1}$, p39$^{E15-2}$, p39$^{E7-2}$, p39$^{E4-1}$, p39$^{E1-1}$, p39$^{E12-2}$ and p39$^{E12-3}$. p39$^{E}$ was derived by cloning the approx 3.6 kb XmaIII restriction fragment. The end of each deletion is marked with "[". Putative transcription factor binding sites are marked Sp-1, Ap-1, Ets. The putative transcription start site is marked with a hooked arrow. Size markers to the left of the figure are relative to this putative transcription start site.

FIG. 2

EGP-2 promoter analysis. Deletion mutants of the EGP-2 promoter were fused to the EGFP (enhanced green fluorescent protein) and transfected into non-epithelial cells, ie FLF (human fetal lung fibroblasts) and HUVEC (human umbilical vein endothelial cells) or epithelial cells SW948 (human colorectal carcinoma) or as a transfection and expression control into COS-7 cells (immortalised kidney epithelial cells derived from the African Green Monkey). Construct names (of FIG. 1) are given above the line that represents the promoter. The numbers indicate the distance from the putative transcription start site that was given by Linnnenbach et al (1993). In the figure this transcription start site is denoted as 1.

Constructs p39$^{E12-2}$ and p39$^{E12-3}$ gave virtually no transcription in all cells types that were tested, while p39$^{E11-1}$ only gave a marginal expression in all lines tested. Thus p39$^{E11-1}$ contains the basic minimal promoter that can bind the RNA polymeraseII complex. Complete epithelium specific expression was found upon transfection with fusion constructs containing at least 778 bp upstream of the putative transcription start site ie p39$^{E4-1}$ comprises binding sites for epithelium specific transcription factors.

Similarly, constructs containing the promoter sequences from p39E (approx 3.4 kb upstream) fused to the luciferase gene, the EPG-2 cDNA sequence, the Cytosine Deaminase (CD) gene showed epithelium specific expression in the same cell types as mentioned above.

---

The invention claimed is:

1. An isolated or recombinant nucleic acid sequence comprising a promoter region comprising nucleotides 3200 to 3556 of SEQ ID NO:5, wherein said nucleic acid sequence allows expression of a nucleic acid sequence of interest operably linked to said promoter in a cancer cell in an epithelium-selective manner.

2. The isolated or recombinant nucleic acid sequence according to claim 1 wherein said cancer cell is a lung carcinoma cell.

3. The isolated or recombinant nucleic acid sequence according to claim 1 of human origin.

4. The isolated or recombinant nucleic acid sequence according to claim 1 further comprising a nucleic acid of interest.

5. The isolated or recombinant nucleic acid sequence according to claim 1 wherein said promoter region is inducible or suppressible.

6. The isolated or recombinant nucleic acid sequence according to claim 1 further comprising a suicide gene or functional fragment of a suicide gene.

7. An isolated or recombinant vector comprising the nucleic acid sequence according to claim 1.

8. A gene delivery vehicle comprising the isolated or recombinant nucleic acid sequence according to claim 1.

9. The isolated or recombinant nucleic acid sequence according to claim 4 wherein said nucleic acid of interest is a suicide gene.

10. The isolated or recombinant nucleic acid sequence in accordance with claim 9 wherein said suicide gene is thymidine kinase or cytosine deaminase.

11. An isolated host cell comprising the vector according to claim 7.

* * * * *

UNITED STATES PATENT AND TRADEMARK OFFICE
CERTIFICATE OF CORRECTION

PATENT NO. : 7,417,137 B2  Page 1 of 1
APPLICATION NO. : 10/009579
DATED : August 26, 2008
INVENTOR(S) : Lou Franciscus M. H. de Leij et al.

It is certified that error appears in the above-identified patent and that said Letters Patent is hereby corrected as shown below:

On the cover page, at the § 371 (c)(1), (2), (4) Date section, the date should read as follows:

Mar. --22--, 2002

Signed and Sealed this

Thirtieth Day of December, 2008

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(24)

<400> SEQUENCE: 1
ataataatcg tcaatgccag tgta                                              24

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(23)

<400> SEQUENCE: 2
atcataaagc ccatcattgt tct                                               23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(23)

<400> SEQUENCE: 3
tcagataaag gagatgggtg aga                                               23

<210> SEQ ID NO 4
<211> LENGTH: 23
```

-continued

```
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(23)

<400> SEQUENCE: 4
ggcagctttc aatcacaaat cag                                              23

<210> SEQ ID NO 5
<211> LENGTH: 4282
<212> TYPE: DNA
<213> ORGANISM: Homo sapiens
<220> FEATURE:
<221> NAME/KEY: misc_feature
<222> LOCATION: (1)..(4282)
<223> OTHER INFORMATION: /note="EGP-2 promotor sequence from -3967 to
      +315"

<400> SEQUENCE: 5
agatctagaa tagagaggga tttgctgcat agtggttaag gactttttact cttcattcta      60 tataaaggac ttttgttttc tactcatcta ttacttatgg gataacaaaa attttttagaa    120 ctggtagtct aattttatat atatatatat atatatatat atatatatat atatatatat    180 atatatttt ttttttttt ttttagacag agttttgctc ttgttgccca ggctggagtg       240
caatggcatg atcttcgctc accacaacct ccgcctcctg ggttcaagtg attctcctgc    300
ctcagcctcc caagtatctg gaattacagg catgtgccac catgcccagc taatttttat    360 attttttagta gagacaggtt ttcaccaggt tgcccaggct gctctcaaac tcctgacctc    420
aagtgatcca cccgctttgg cctcccaaag tgctgggatt acaggcgtga ccaccatgc    480 ctagcctgaa atattaata atgtgcttta aatatggcac tagaactaca aaagattcac      540
aattaaaaca taaaacgagt aattttgagc aaagaatgac aaattgagaa ggtgttaatg    600
aggtactaaa ataacaata ccggccggtg cagtggctca tgcctgtaat cccagcactt    660
tgggaagctg aggcgggtgg atcacctgag gtcaggagtt caagaccagc ctggccaacg    720
tagtgaaacc cggtctctac taaaaataca aaaattagcc gggcgaggtg caggcgcct    780 gtaatcacag ctactcggga ggctgagaca ggagaattgc ttgaacccag gaggtggagg    840
ttgcagtgag ctgagaacac gccattgtac tccagcctgg gtaacaagat tgaaactcta    900
tcttaaaaaa aaaaaaaagg cggacacggt ggcttcacc tgtaatccca gcactttggg    960
aggccgaggc aagaggatca caaagtcagg agatcaagac catcctggcc aacatggtga   1020
aactctgtct caactgaaaa tacaaaaatt agccgggtgt ggtggtgggc gcctgtaatc   1080
ccagctattc aggaggctga ggcaggagaa ttgcttgaac ccaagaggtg gaggttgcag   1140
tccgccaaga tcatgccact gcactgcagc ttgggtgaca gagcaagacc ccatctcaaa   1200
aaaaaaaaaa aagaaaaaat accctggatc agccgggtgt ggtggctcaa gcctgtaatc   1260
ccagcacttt gggaggctga ggtgggcaga tcacctgagg tcaggagttc aagaccagcc   1320
tgaccaacat ggagaaaccc catctctact aaaaatacaa aaattagcc ggacgtggtg    1380 gcacatgctt gtaatcccag ctactcagga ggctgaggca ggagaattgc ctgaatccgg   1440
gaggcggagg ttgtggtgag gtgagatgat gccattgcac tccagcctgg gcaacaagag   1500
caaaactctg cctcaaaaaa agaaagaaaa aaaaaaaaga aagaaagaa aaatacccct    1560 ggatgtatac tcagatacaa tgagtcagag attagtctgg tattttgtca tttatttaat   1620
```

```
aattatgctt actcaattca ctttattgta attaacaata aatagctgtc cagttataag    1680
aagatgaagt tctcccgatt aggtaaacag atttagacct cagaatggaa cattttgcca    1740
ataaagccac aataaccagt tagtttattc ttgggaaaag tatatgtaat ttggagaaag    1800
gcaaacttcc tgaaaacatc caaaattcag cagacaacaa aaatctggtt aacttgttcc    1860
tgatttgtta gtactattct ttttttttg tttgtttgtt ttttttttt gagacggagt      1920
ttcgctcttg ttgcccaggc tggagtgcaa tggcgaaatg ttggttcact gcaacctctg    1980
cctcccaggt tcaagtgatt ctcctgcctc agtctcctga gtagctggga ttacaggcgc    2040
ccgccaccac gcctggctaa cttcttgtat ttttagtaga cggggtttt caccatgttg     2100
gccaggctgg tctcgaactc ctgaccttag gtgatccgcc cgcctcggcc tcccaaagtg    2160
ctgagattac aggcatgagc caccgtacct ggcctaaata ccttatttca tataccacgt    2220
gaaatttaaa ttatacaaaa caaattatag aggtacttag aacagcatga ctatttacat    2280
taatcaactt gccggcactt caacagaata caacatagaa atgattgttt taatataaac    2340
ataagctttg atttgacata tacttgtaga aattaatcaa acttagctga atcttaaaat    2400
tgctttttta cctttcctct tttttttta tttttttatt ttttgagatg gagtcttgct     2460
ctgttgccag actggagtgc agcggtttgg tctcggctca ccgcaacctc cgactctctg    2520
gttcaagcga ttctcctgcc tcagcctcct gagtagctgg gattacaggt gcctgccacc    2580
acacctggct actttttgta tttttagttg agatgggttt caccatgttg gccaggatgg    2640
tctcgaactc ctgacctcgg atctgcccac ctgtgccccc agcaaggtgc tgggattaca    2700
agcatgagcc accgtgccca gcctcctttc ctctttttaa ctcttacttt tatgatttct    2760
ttagtggata aaaagctttt aaaaaatagg ttacaatgat attacagcta acaaaaaata    2820
acatttaaaa acactaaata gtatatatat gaagtattta taattatttt aatattgtaa    2880
taatatagtg tgttgtgatt tgaattcatc tgcacggaaa tcgattactg tccttctctt    2940
ctatttccct atattttctt tccgaagcgt catcaacatt ttggttcttt aatagtaacc    3000
aaaacccgaa atcatctcgg ttctcagtat ttggctctat gggaacacct ttctttttct    3060
ctctttttt tttttttga cggagtct tgctcctgtc gcccaggctg gagtgtaatg        3120
gcacgatctc tgctcactgc aacctcagcc tccccagtag ctgggattac aggcatgcgc    3180
caccacgccc ggctaatttt gtatctttta gtagagacgg cgttcctcca tgttggtcag    3240
gctggtctcg aacttcaaac ctcaggtgat ccgcccgcct cggcctccca aagtgctagg    3300
attacaggcg tgagccaccg cgctcagcct gggaacacct ttcttacat cttcaagtgc     3360
tagaaatgct tatgaaaacg aaaaaagaat tattaagagt aattataaag aaacactcat    3420
tttcttccca agagagccaa gatttcttct ttcctcttct ttctttttt tttctttcta     3480
atttcaaagg agtataatta aattgccagg taaaagctca aggtctttt ttatagtgtt     3540
ctggaaggtt ctctgcctgt gtttgtattt cctttagcct ccacgttcct ctatccagtt    3600
cccgcaccct tcccccagg ccccattctt caaggcttca gagcagcgct cctccggtta     3660
aaaggaagtc tcagcacaga atcttcaaac ctcctcggag gccaccaaag atccctaacg    3720
ccgccatgga gacgaagcac ctggggcggg gcggagcggg gcgcgcgggc ccacacctgt    3780
ggagagggcc gcgcccaac tgcagcgccg gggctggggg aggggagcct actcactccc     3840
ccaactcccg ggcggtgact catcaacgag caccagcggc cagaggtgag cagtcccggg    3900
aaggggccga gaggcgggc cgccaggtcg ggcaggtgtg cgctccgccc cgccgcgcgc     3960
acagagcgct agtccttcgg cgagcgagca ccttcgacgc ggtccgggga cccctcgtc    4020
```

```
gctgtcctcc cgacgcggac ccgcgtgccc caggcctcgc gctgcccggc cggctcctcg    4080
tgtcccactc ccggcgcacg ccctcccgcg agtcccgggc ccctcccgcg cccctcttct    4140
cggcgcgcgc gcagcatggc gcccccgcag gtcctcgcgt tcgggcttct gcttgccgcg    4200
gcgacggcga cttttgccgc agctcaggaa ggtgaggcgc ggattggagc agagttgtgg    4260
agctgggctg ggctgggggg ca                                             4282
```